United States Patent [19]

Ghahramani

[11] 4,215,566

[45] Aug. 5, 1980

[54] DENSITOMETER WITH VOLTAGE DRIVER

[75] Inventor: Iraj Ghahramani, Los Angeles, Calif.

[73] Assignee: International Telephone and Telegraph Corporation, New York, N.Y.

[21] Appl. No.: 34,300

[22] Filed: Apr. 30, 1979

[51] Int. Cl.³ ............................................... G01N 9/34
[52] U.S. Cl. .................................................. 73/32 A
[58] Field of Search ................... 73/32 A, 576, 30, 578

[56] References Cited

U.S. PATENT DOCUMENTS

| 3,677,067 | 7/1972 | Miller et al. .......................... 73/32 A |
| 3,878,374 | 4/1975 | Schlatter ........................ 73/32 A X |

Primary Examiner—Jerry W. Myracle
Attorney, Agent, or Firm—A. Donald Stolzy

[57] ABSTRACT

A vibration densitometer having a magnetostrictive drive with a coil and a crystal pickup. A loop circuit including a driver amplifier provides the coil with a voltage twice that ordinarily provided. Further, the driver amplifier is unusually small, inexpensive and accurate.

5 Claims, 6 Drawing Figures

DENSITOMETER WITH VOLTAGE DRIVER

BACKGROUND OF THE INVENTION

This invention relates to densitometers, and more particularly to a voltage drive for the coil of a vibration densitometer probe.

In the past, densitometers have been large, expensive and inefficient because they have employed combination voltage and current drives of various phases.

PRIOR ART STATEMENT

Combination voltage and current drives of various phases are disclosed in U.S. Pat. No. 3,878,374 issued Apr. 15, 1975.

A permanent magnet biased 90 degrees leading current drive is disclosed in copending application Ser. No. 837,454, filed Sept. 28, 1977, by P. Z. Kalotay and I. Ghahramani for Densitometer.

Another current drive is disclosed in copending application filed on or about June 30, 1978, by I. Ghahramani for Densitometer Drive (I. Ghahramani 2) now U.S. Pat. No. 4,151,743, issued May 1, 1979.

Still another driver is disclosed in copending application Ser. No. 010,021, filed Feb. 7, 1979, by I. Ghahramani for Voltage-to-Current Converter.

SUMMARY OF THE INVENTION

In accordance with the driver of the present invention, prior art disadvantages are overcome by providing a driver amplifier means with a noninverting input having a substantially fixed regulated voltage. A resistor is connected in series with the noninverting input. The amplifier means output is connected to each end of the resistor via a second resistor and the densitometer drive coil, the second resistor being connected directly to the inverting input.

It is an advantage of the present invention that the coil is supplied with a voltage twice as large as that of the regulated source.

BRIEF DESCRIPTION OF THE DRAWINGS

In the accompanying drawings which illustrate exemplary embodiments of the present invention.

DESCRIPTION OF THE PREFERRED EMBODIMENT

Figure 1:
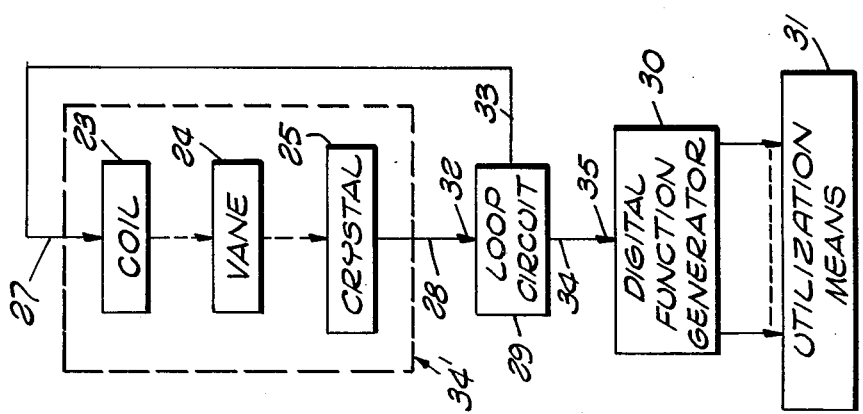
FIG. 1 is a block diagram of a densitometer constructed in accordance with the present invention.

In the drawings, in FIG. 1, a vibration densitometer probe is indicated at 34' having a driver coil 23, a vane 24, and a piezoelectric crystal 25.

Probe 34' has an input lead 27 and an output lead 28.

Other blocks shown in FIG. 1 are a loop circuit 29, a digital function generator 30 and utilization means 31. Loop circuit 29 has an input lead 32 connected from probe output lead 28, and output leads 33 and 34. Digital function generator 30 has an input lead 35 connected from loop circuit output lead 34. The output of digital function generator 30 is connected to utilization means 31.

The input lead 27 of probe 34' is connected from the output lead 33 of loop circuit 29. Probe 34' and loop circuit 29 form a closed loop electromechanical oscillator. Vane 24 is submerged in a fluid. The density of the fluid is a function of the frequency at which vane 24 vibrates.

Digital function generator 30 may have its input lead 35 connected from lead 33 or at other points in loop circuit 29. Loop circuit 29 impresses a square wave voltage on input lead 35 of digital function generator 30.

Utilization means 31 shown in FIG. 1 may be a density indicator, a specific gravity indicator, a process controller or otherwise.

The disclosure of the following patents are hereby incorporated herein by this reference hereto:
(1) U.S. Pat. No. 3,677,067, issued July 18, 1972.
(2) U.S. Pat. No. 3,706,220, issued Dec. 19, 1972.
(3) U.S. Pat. No. 3,738,155, issued June 12, 1973.
(4) U.S. Pat. No. 3,741,000, issued June 26, 1973.
(5) U.S. Pat. No. 3,878,374, issued Apr. 15, 1975.

Probe 34' shown in FIG. 1 may be conventional. For example, it may or may not be identical to that disclosed in U.S. Pat. No. 3,878,374. Alternatively, probe 34' may be similar to or identical to a probe shown in any of the patents above cited.

Probe 34', digital function generator 30 and utilization means 31 may be similar to or identical to corresponding ones in said U.S. Pat. No. 3,878,374. Loop circuit 29 is not.

Figure 2:
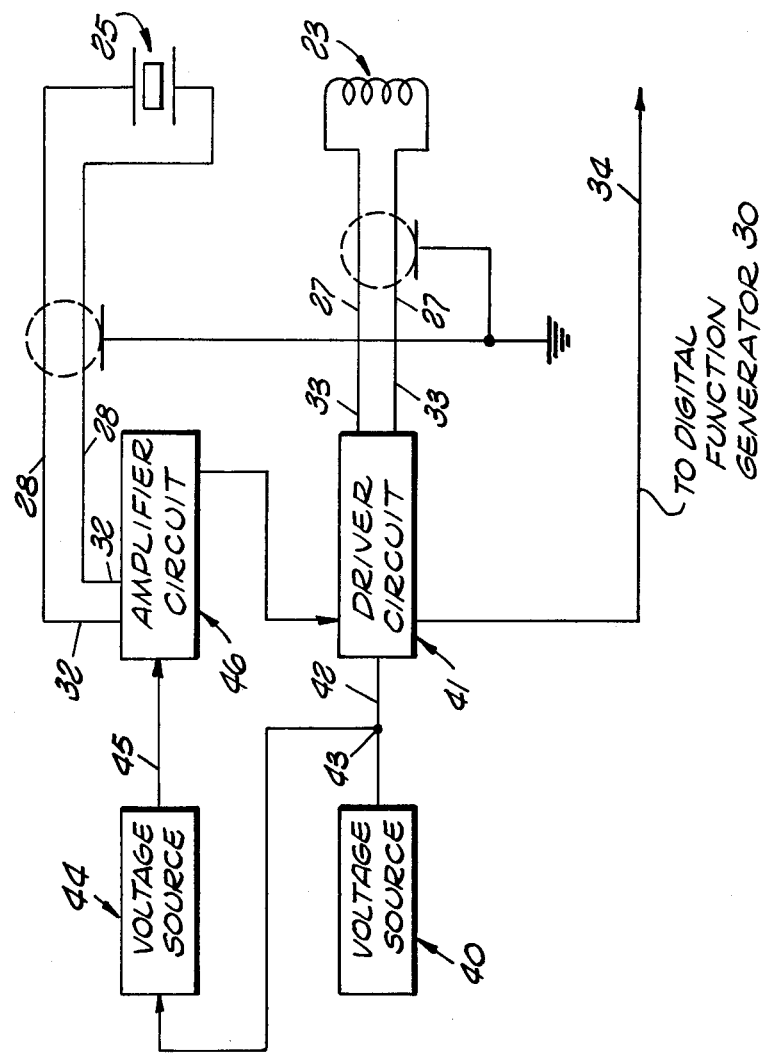
FIG. 2 is a somewhat more detailed block diagram of a loop circuit shown in FIG. 1.

In FIG. 2, a voltage source 40 supplies voltage to a driver circuit 41 over a lead 42 through a junction 43. Source 40 also supplies the voltage from junction 43 to a voltage source 44. Voltage source 44 is connected over lead 45 to an amplifier circuit 46. Amplifier circuit is connected from crystal 25 as before. The output of amplifier circuit 46 is connected to driver circuit 41. Driver circuit 41 is connected to coil 23 and to digital function generator 30 over lead 34 as before.

Figure 3:
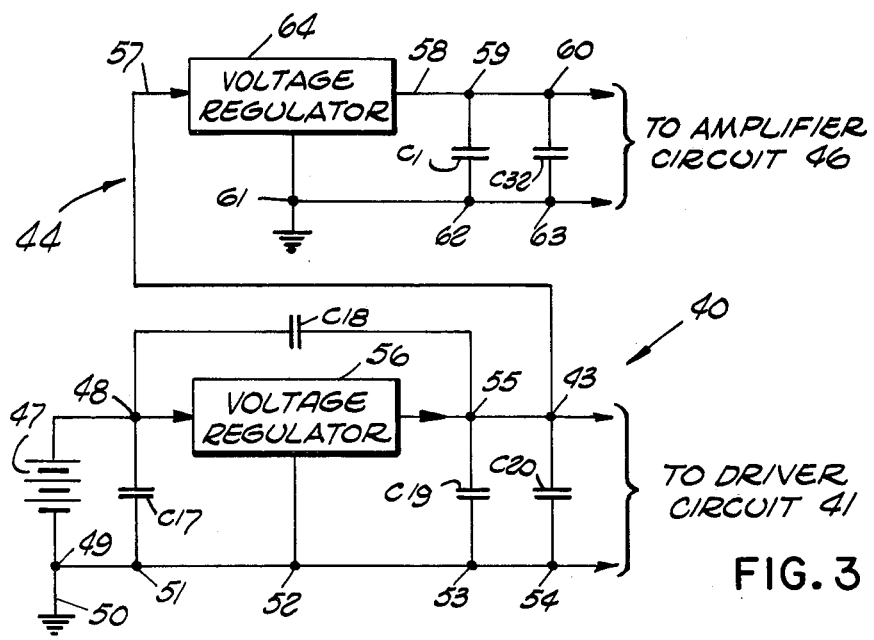
FIG. 3 is a still more detailed block diagram of two voltage sources shown in FIG. 2.

Source 40 is shown again in FIG. 3 connected to source 44 from junction 43.

Source 40 includes a source of potential 47 connected between junctions 48 and 49, junction 49 being grounded at 50.

Junctions 51, 52, 53 and 54 are connected from junction 49 and to the ground connection of driver circuit 41.

A junction is provided at 55. A capacitor C18 is connected between junctions 48 and 55. A capacitor C17 is connected between junctions 48 and 51. A capacitor C19 is connected between junctions 53 and 55. A capacitor C20 is connected between junctions 43 and 54, junction 43 being connected to the positive regulated input to driver circuit 41 and to the input to source 44.

A voltage regulator 56 is connected from junction 48 to junction 55 and from junction 52.

Source 44 has an input lead 57 connected from junction 43, and an output lead 58 connected to junctions 59 and 60, junction 60 providing a regulated positive potential for an input to amplifier circuit 46.

Source 44 also has junctions 61, 62 and 63 connected together and to the grounded input of amplifier circuit 46, junction 61 also being connected to a voltage regulator 64 and to ground.

A capacitor C1 is connected between junctions 59 and 62. A capacitor C32 is connected between junctions 60 and 63.

Figure 4:
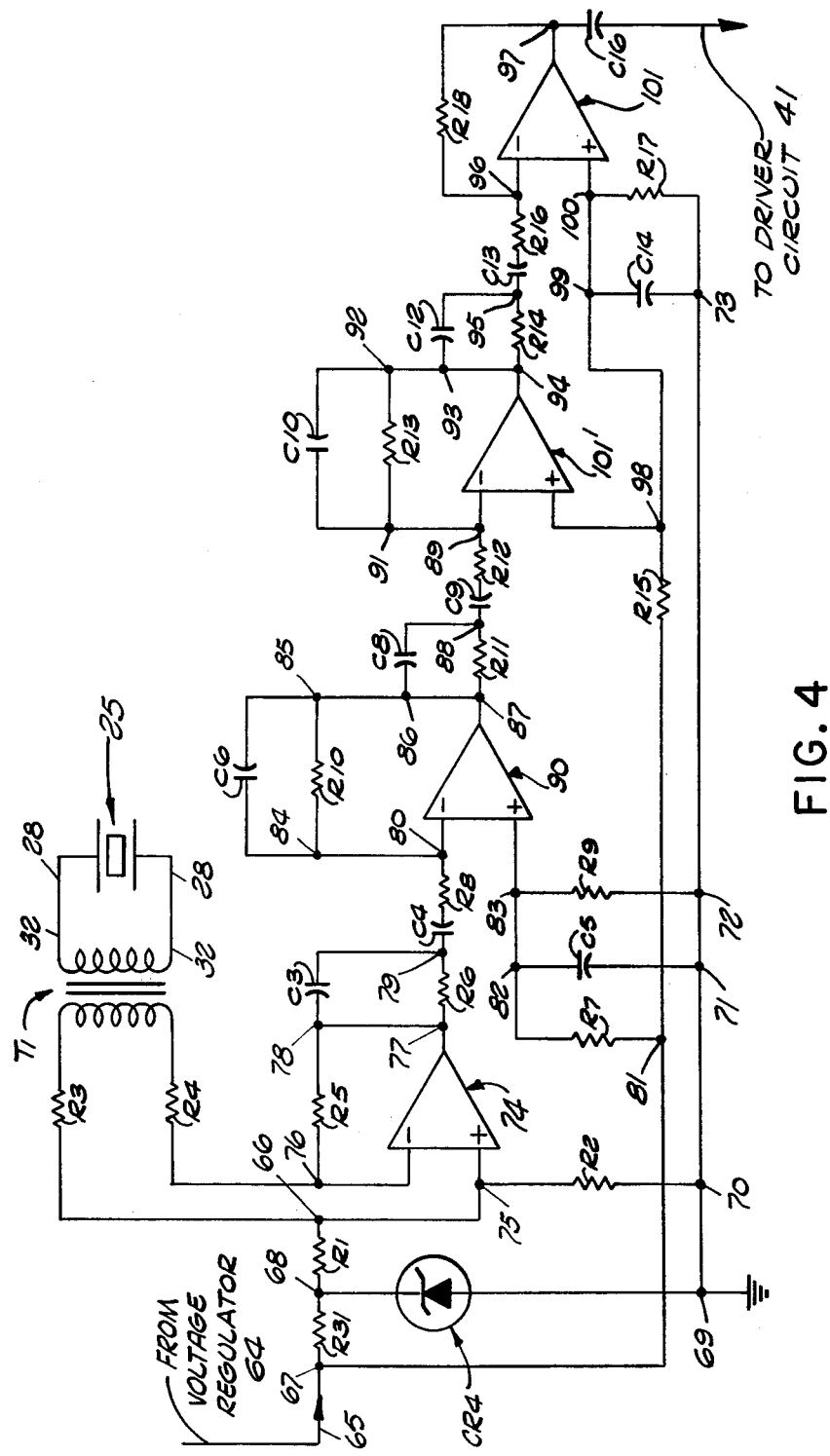
FIG. 4 is a schematic diagram of an amplifier circuit shown in FIG. 2.

Amplifier circuit 46 is shown in FIG. 4 including an input lead 65 connected from voltage regulator 64 to a junction 66. Lead 65 is connected to a junction 67. Junction 67 is connected to junction 66 through a resistor R31, a junction 68 and a resistor R1.

The zener diode CR4 is connected from junction 68 to a junction 69, junction 69 being grounded. Junctions 70, 71, 72 and 73 are likewise grounded.

An output of crystal 25 is connected across an operational amplifier 74 through a transformer T1 having resistors R3 and R4 connected in series with the output leads thereof to junctions 75 and 76, respectively. Junction 75 is connected to the noninverting input of amplifier 74. Junction 76 is connected to the inverting input of amplifier 74. The output of amplifier 74 is connected to a junction 77. Junction 77 is connected to a junction 78. A feedback resistor R5 is connected between junctions 76 and 78.

A junction 79 is also provided. A capacitor C3 is connected between junctions 78 and 79. A resistor R6 is connected between junctions 77 and 79. A capacitor C4 and a resistor R8 are connected in succession in that order from junction 79 to a junction 80. Junctions 81, 82, 83, 84, 85, 86, 87, 88 and 89 are additionally provided.

A resistor R7 is connected between junctions 81 and 82. A capacitor 75 is connected between junctions 71 and 82. A resistor R9 is connected between junctions 72 and 83. An operational amplifier is provided at 90. Junction 83 is connected to the noninverting input of amplifier 90. Junction 80 is connected to the inverting input of amplifier 90. A resistor R10 and a capacitor C6 are connected in parallel from junction 84 to junction 85. Junctions 85, 86 and 87 are connected together.

A capacitor C8 is connected from junction 86 to junction 88. A capacitor C9 and a resistor R12 are connected in succession in that order from junction 88 to junction 89. Further junctions 91, 92, 93, 94, 95, 96, 97, 98, 99 and 100 are provided. A fourth operational amplifier 101 is also provided. A noninverting input of an operational amplifier 101 is connected from junction 67 through a resistor R15 and through a junction 98. The inverting input of amplifier 101 is connected from junction 89.

The noninverting input of amplifier 101 is connected from junction 98 through junctions 99 and 100.

A capacitor C14 is connected between junctions 73 and 99. A resistor R17 is connected between junctions 73 and 100.

A resistor R18 is connected from the output of amplifier 101 to junction 96. The inverting input of amplifier 101 is connected to junction 96.

Figure 5:
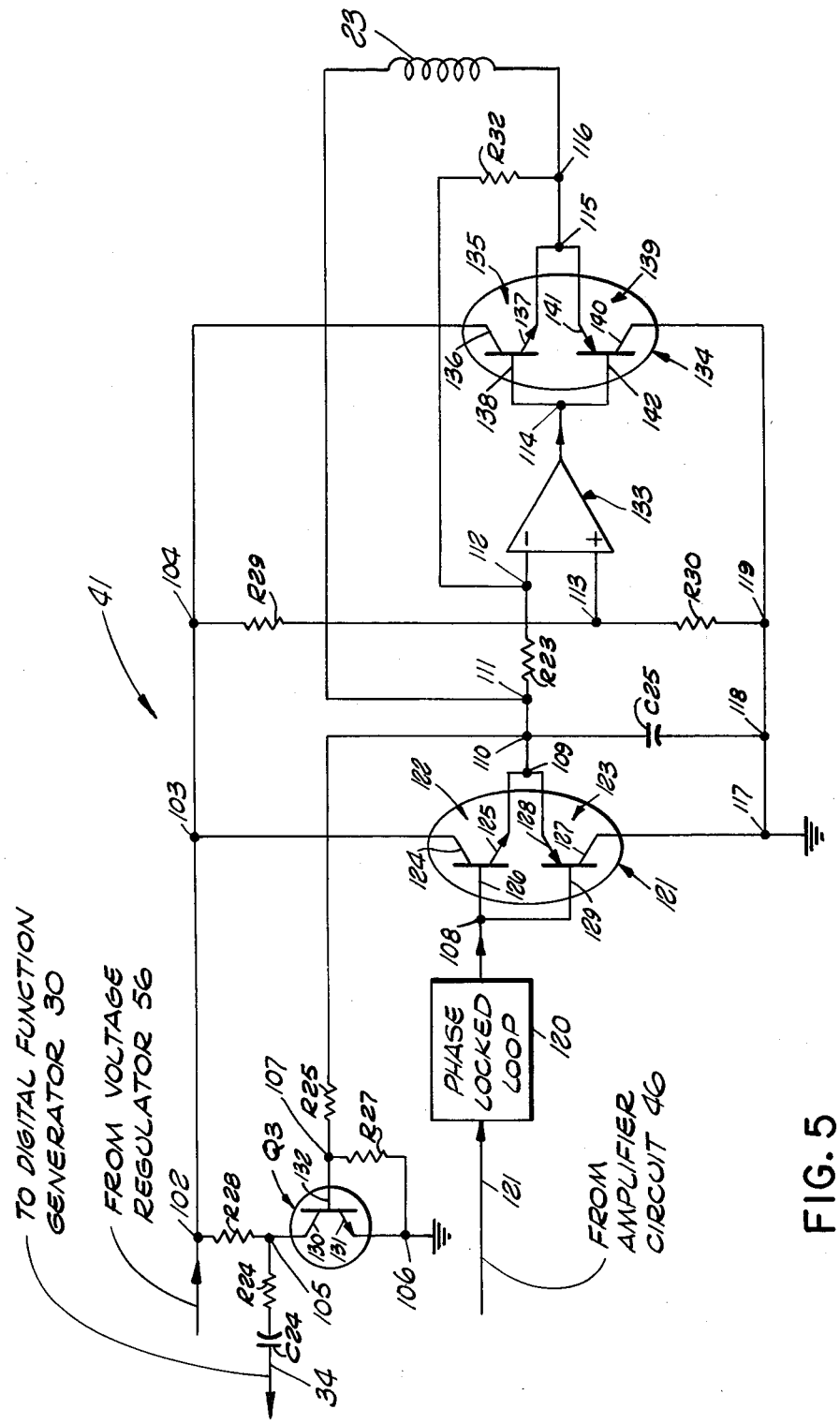
FIG. 5 is a schematic diagram of a driver circuit shown in FIG. 2.

The output of amplifier circuit 46 shown in FIG. 4 is connected to a driver circuit 41 shown in FIGS. 2 and 5 from the output of amplifier 101 at junction 97 via capacitor C16 shown in FIG. 4.

Driver circuit 41 is shown in FIG. 5 as junctions 102, 103, 104, 105, 106, 107, 108, 109, 110, 111, 112, 113, 114, 115, 116, 117, 118 and 119. Junctions 102, 103 and 104 are connected from voltage regulator junction 43 shown in FIG. 3.

In FIG. 5, a phase locked loop is provided at 120 which has an input lead 121 connected from capacitor C16 shown in FIG. 4. The output of phase locked loop 120 is connected to a buffer 121 which contains an NPN transistor 122 and a PNP transistor 123.

Transistor 122 has a collector 124 an emitter 125 and a base 126.

Transistor 123 has a collector 127, an emitter 128 and a base 129.

Bases 126 and 129 are connected together at junction 108 which is connected from the output of phase locked loop 120.

Collector 124 is connected to junction 103. Collector 127 is connected to junction 117. Junction 117 is connected to ground. Junctions 117, 118 and 119 are connected together.

Emitters 125 and 128 are connected together at a junction 109. Junctions 109, 110 and 111 are connected together.

A transistor Q3 and its circuit provide an amplifier or an output signal of buffer 121, the same being connected from loop circuit 29 to digital function generator 30 from junction 110 via a resistor R25. Resistor R25 is connected between junctions 107 and 110. A resistor R27 is connected between junctions 106 and 107. Junction 106 is grounded. Transistor Q3 has a collector 130 an emitter 131 and a base 132. Base 132 is connected from junction 107. Collector 130 is connected to junction 105. Emitter 131 is connected to junction 106.

A resistor R24 is connected in series with a capacitor C24 from junction 105 to lead 34.

A capacitor C25 is connected between junctions 110 and 118.

An operational amplifier is provided at 133 having noninverting and inverting inputs connected respectively from junctions 113 and 112.

A resistor R23 is connected between junctions 111 and 112. A resistor R29 is connected between junctions 104 and 113. A resistor R30 is connected between junctions 113 and 119.

A second buffer 134 is connected from the output of amplifier 133 at junction 114. Buffer 134, as before, is provided with an NPN transistor 135 having a collector 136, an emitter 137 and a base 138.

Buffer 134 also has a PNP transistor 139 with a collector 140, an emitter 141 and a base 142.

As before, bases 138 and 142 are connected from junction 114. Also, emitters 137 and 141 are connected to junction 115.

Collector 136 is connected from junction 104. Collector 140 is connected to junction 119.

Junctions 115 and 116 are connected together. A resistor R32 is connected between junctions 112 and 116. Coil 23 is connected between junctions 111 and 116.

OPERATION

In accordance with the driver circuit 41 of the present invention, a high and appropriate voltage is supplied to coil 23. The manner in which this is done can perhaps best be explained from FIG. 6.

Figure 6:
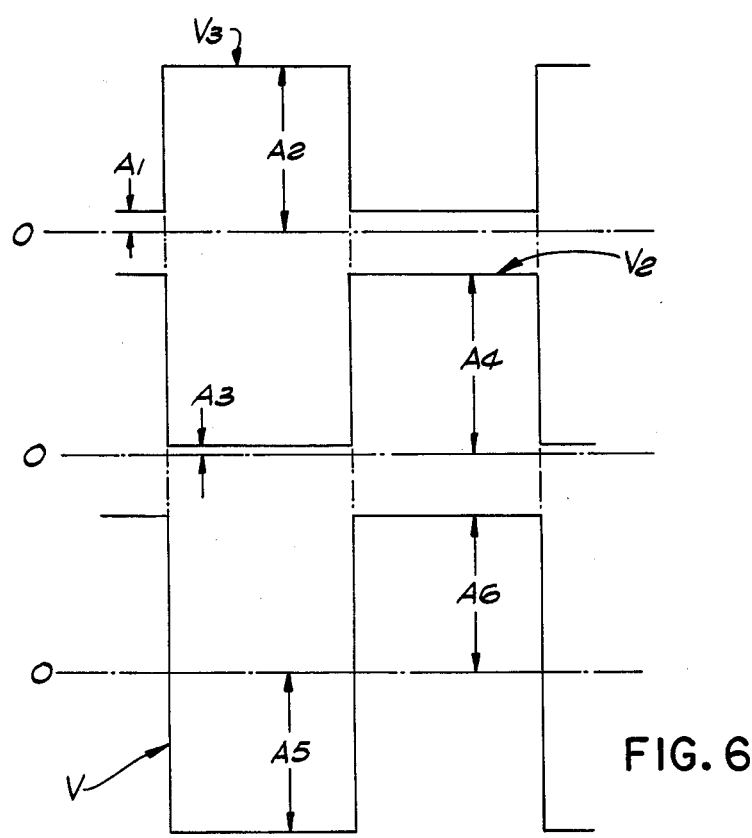
FIG. 6 is a graph of a group of waveforms characteristic of the portion of a driver circuit constructed in accordance with the present invention.

In FIG. 6, the voltage appearing at junction 111 may be a square wave as illustrated at $V_3$. The voltage appearing at junction 116 may be that as shown at $V_2$. The voltage across coil 23 then is $V_2-V_3$ which may be equal to V as shown in FIG. 6. The relative amplitudes of the waveforms shown in FIG. 6 may be as follows:

$A_1 = 1.7$ volts $A_2 = 13.3$ volts

A3 = 0.7 volts

A4 = 14.3 volts

A5 = −12.6 volts

A6 = +12.6 volts

In FIG. 6 note will be taken that waveform V swings a total of about 25.2 volts, whereas waveforms $V_3$ and $V_2$ clearly swing less than 14 volts. Thus, coil 23 can be supplied with a substantial drive, such voltage drive even exceeding the output of source 40 in FIG. 2. The output of source 40 in FIG. 2 may be about 15 volts, whereas source of potential 47 in FIG. 3 may be from 18 to 35 volts, D.C.

Some circuit elements employed in FIGS. 3, 4 and 5 may be as follows:

| Zener diode CR 4 | | 1N823A |
| --- | --- | --- |
| Capacitors | | |
| (Capacitance values are in microfarads unless otherwise indicated.) | | |
| C1 | 0.1 | |
| C3 | 33 | nanofarads |
| C4 | 1.0 | |
| C5 | 10 | |
| C6 | 1 | nanofarad |
| C8 | 33 | nanofards |
| C9 | 1.0 | |
| C10 | 1 | nanofarad |
| C12 | 33 | nanofarads |
| C13 | 1.0 | |
| C14 | 10 | |
| C16 | 0.22 | |
| C17 | 10 | |
| C18 | 4.7 | |
| C19 | 33 | |
| C20 | 0.1 | |
| C24 | 1.0 | |
| C25 | 2.2 | nanofarads |
| C32 | 33 | |

| Resistors | | |
| --- | --- | --- |
| (Resistance values are in ohms ± 1% 1/8 w.) | | |
| R1 | 1.5 | M |
| R2 | 1.5 | M |
| R3 | 750 | K |
| R4 | 750 | K |
| R5 | 750 | K |
| R6 | 182 | K |
| R7 | 100 | K |
| R8 | 10 | K |
| R9 | 100 | K |
| R10 | 100 | K |
| R11 | 182 | K |
| R12 | 1 | K |
| R13 | 100 | K |
| R14 | 182 | K |
| R15 | 100 | K |
| R16 | 1 | K |
| R17 | 100 | K |
| R18 | 576 | K |
| R23 | 3.4 | K |
| R24 | 1 | K |
| R25 | 3.9 | K |
| R27 | 1 | K |
| R28 | 2 | K |
| R29 | 2.49 | K |
| R30 | 2.49 | K |
| R32 | 35.7 | K |

| Transistors | |
| --- | --- |
| Q3 | 2N2222 |

What is claimed is:

1. A vibration densitometer comprising: a probe including a vibratable vane, an electromagnetic drive coil energizable to vibrate said vane, and a piezoelectric crystal fixed relative to one portion of said vane to produce an output signal in phase with the vibration of said vane; a loop circuit connected from said crystal to said coil to impart vibration to said vane, said loop circuit including an amplifier circuit connected from said crystal, and a driver circuit connected from said amplifier circuit to said coil; a digital function generator connected from said loop circuit to produce an output directly proportional to the density of a fluid in which said vane is immersed; and utilization means connected from said digital function generator to utilize the output of said digital function generator, said driver circuit including amplifier means having inverting and noninverting inputs, means to maintain said noninverting input at a substantially constant voltage, first and second junctions, said amplifier circuit being connected to said first junction, a first resistor connected between said first and second junctions, said inverting input being connected from said second junction, means including a third junction connected from the output of said amplifier means to one end of said coil, the other end of said coil being connected to said first junction, a second resistor connected from said one coil end to said second junction.

2. The invention as defined in claim 1, wherein a phase locked loop, and a first buffer are connected in succession from said amplifier circuit to said first junction, said loop circuit including a regulated voltage source, said first buffer being connected across said source, said first buffer including an NPN and a PNP transistor connected in series across said regulated source, said NPN transistor having a collector, an emitter and a base, said PNP transistor having a collector, an emitter and a base, said bases of said first buffer transistors being connected together from the output of said phase locked loop, said first buffer emitters being connected together and to said first junction, said first buffer collectors being connected across said regulated source, said amplifier means including an operational amplifier and a second buffer substantially the same as said first buffer, said second buffer including an NPN transistor having a collector, an emitter and a base, and a PNP transistor with a collector, an emitter and a base, said second buffer emitters being connected to said third junction, one end of each of said second resistor and said coil being connected from said third junction, the output of said operational amplifier being connected to said second buffer bases, third and fourth resistors connected in series across said regulated source, the resistance of said third resistor being equal to that of said fourth resistor, the mutual junction of said third and fourth resistors being connected to the noninverting input of said operational amplifier, said second buffer collectors being connected across said regulated source.

3. The invention as defined in claim 2, wherein said digital function generator is connected from said first junction.

4. The invention as defined in claim 3, wherein an auxiliary amplifier is provided, said auxiliary amplifier being connected from said first junction to said digital function generator.

5. The invention as defined in claim 4, wherein a capacitor is connected from said first junction to said PNP transistor collectors.

* * * * *